(12) United States Patent
Roos et al.

(10) Patent No.: US 6,730,510 B2
(45) Date of Patent: May 4, 2004

(54) CULTURE DISH AND BIOREACTOR SYSTEM

(75) Inventors: Eric Roos, Grafton, MA (US); Christopher O'Reilly, Middleboro, MA (US); Ruben Chevere, North Attleboro, MA (US); Leon M. Wilkins, North Andover, MA (US)

(73) Assignee: Organogenesis, Inc., Canton, MA (US)

( * ) Notice: Subject to any disclaimer, the term of this patent is extended or adjusted under 35 U.S.C. 154(b) by 0 days.

(21) Appl. No.: 10/189,300

(22) Filed: Jul. 2, 2002

(65) Prior Publication Data

US 2004/0005699 A1 Jan. 8, 2004

(51) Int. Cl.[7] .................................. C12M 1/34
(52) U.S. Cl. ................ 435/288.3; 435/297.5; 435/305.4
(58) Field of Search .......... 435/288.3, 297.5, 435/305.1, 305.3, 305.4

(56) References Cited

U.S. PATENT DOCUMENTS

| | | | |
|---|---|---|---|
| 4,686,190 A | 8/1987 | Cramer et al. | 435/291 |
| 4,871,674 A | 10/1989 | Matsui et al. | 435/284 |
| 5,026,649 A | 6/1991 | Lyman et al. | 435/284 |
| 5,215,920 A | 6/1993 | Lyman et al. | 435/284 |
| 5,358,871 A | 10/1994 | Stevens et al. | 435/284 |
| 5,366,893 A | 11/1994 | Stevens et al. | 435/284 |
| 5,466,602 A | 11/1995 | Lyman et al. | 435/297.1 |
| 5,468,638 A | 11/1995 | Barker et al. | 435/304.1 |
| 5,534,227 A | 7/1996 | Lahm et al. | 422/102 |
| 5,602,028 A * | 2/1997 | Minchinton | 435/401 |
| 5,766,937 A | 6/1998 | Lahm et al. | 435/297.5 |
| 5,795,775 A | 8/1998 | Lahm et al. | 435/297.5 |

\* cited by examiner

Primary Examiner—David A. Redding
(74) Attorney, Agent, or Firm—Hale and Dorr LLP

(57) ABSTRACT

A bioreactor has a base for defining a well, a dish with a membrane suspended in the base, and a lid with gas permeable membranes and self-sealing ports.

19 Claims, 6 Drawing Sheets

CULTURE DISH AND BIOREACTOR SYSTEM

BACKGROUND OF THE INVENTION

This invention relates to a culture dish that can serve as a bioreactor for supporting and feeding living tissue.

Culture dishes may have a well-defining base for holding nutrients, a dish with a bottom wall having a thin membrane that rests in the well and on which there are biological materials, and a solid cover over the well and the dish.

SUMMARY OF THE INVENTION

An embodiment of a bioreactor includes a base that defines a well, a dish supported over the well for holding biological material, and a lid over the well and the dish. The lid includes at least one sealing opening for introducing or removing material from the well or the dish and for pressure relief. The well can be used to hold nutrients, while the dish has a membrane in contact with the nutrients. The lid preferably has at least two sealable openings, with one over the dish, and the other over a portion of the well and not over the dish for introducing and/or removing material from the dish and the well. The lid preferably includes at least one gas permeable membrane for venting. A solid cover can be provided over the lid, such as for storage or shipping. The openings are preferably each a septum that has a slit or multiple slits, such as in an x-shape, to help seal about a syringe or pipette or other suitably sized delivery nozzle.

The embodiments of the present invention allow for convenient external access to the contents in different portions of the bioreactor without requiring removal of the lid. Such accessibility can reduce risks of contamination and make the system less labor intensive and more amenable to automation. Other features and advantages will become apparent from the following detailed description, drawings, and claims.

DETAILED DESCRIPTION

Figure 1:
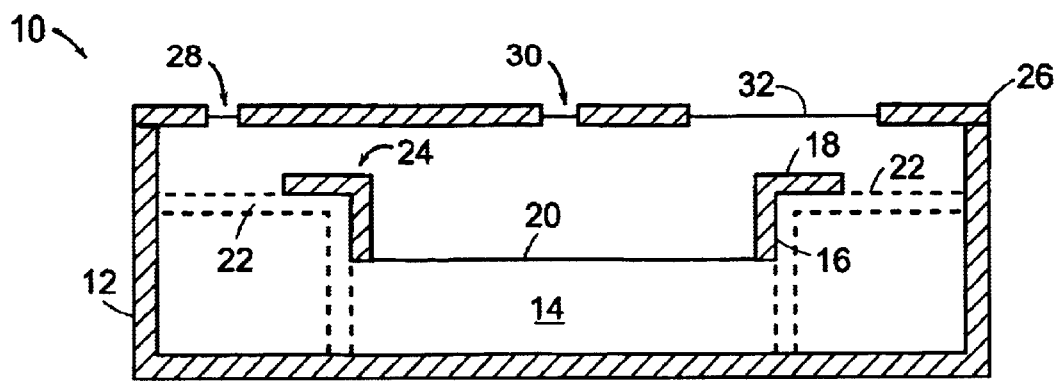
FIG. 1 is a simplified, cross-sectional view illustrating components according to an embodiment of the present invention.

FIG. 1 is a cross-sectional view that illustrates components of an embodiment of the present invention. A bioreactor (10) has a base (12) that defines a well (14). Base (12) also has shelves (22), which are preferably monolithically molded with the rest of the base.

A dish (24) has one or more flanges (18) that rest on shelves (22) in the base (12). At the bottom of dish (24) is a membrane (20), such as a polycarbonate membrane. Cells, tissues, or other living biological material are provided in dish (24) so that the material rests on top of membrane (20). Nutrients are provided in well (14) at least up to the level of membrane (20) such that the nutrients in well (14) are in contact with the biological material through membrane (20).

The structure described to this point is generally known. It is further known to provide a solid lid that covers a dish and a base. Such a lid is removable for providing access to the cells or tissues on a membrane in the dish and also to the nutrients in the well of the base.

According to an embodiment of the present invention, a lid (26) has at least one sealable port, two of which are shown in FIG. 1 as ports (28) and (30), and a moisture barrier, gas permeable membrane (32). Membrane (32) can include a sheet of TYVEK® (TYVEK is a registered trademark of E.I. duPont de Nemours and Company). This sheet has the appearance of paper but is made of spun-bonded high-density polyethylene (HDPE). Membrane (32) allows for venting and is positioned so that it is partly over dish (24) and partly over base (12). While one gas permeable membrane is shown in this FIG. 1, there can be a greater number arranged in the lid as shown below in FIG. 6; membranes could be added if more venting is desired.

Ports (28) and (30) are accessible, but preferably designed to be sealed closed when not in use. These ports allow access to, and can seal around, a needle, syringe, nozzle, or other suitably sized tubular device used to provide or withdraw material. Center port (30) can be used for providing cells or tissues to dish (24). Outer port (28) can be used to introduce or extract nutrients from well (14). The sealing preferably, but not necessarily, occurs automatically, such that when the tube is inserted, the port seals around it without further action being required (i.e., it self-seals).

The following FIGS. 2–12 show an embodiment of the present invention in more detail. Each of the drawings is drawn to scale, although the drawings are not necessarily drawn to the same scale. The figures have a number of particular features, such as shapes and dimensions that are exemplary, but there could be many variations.

Figure 2:
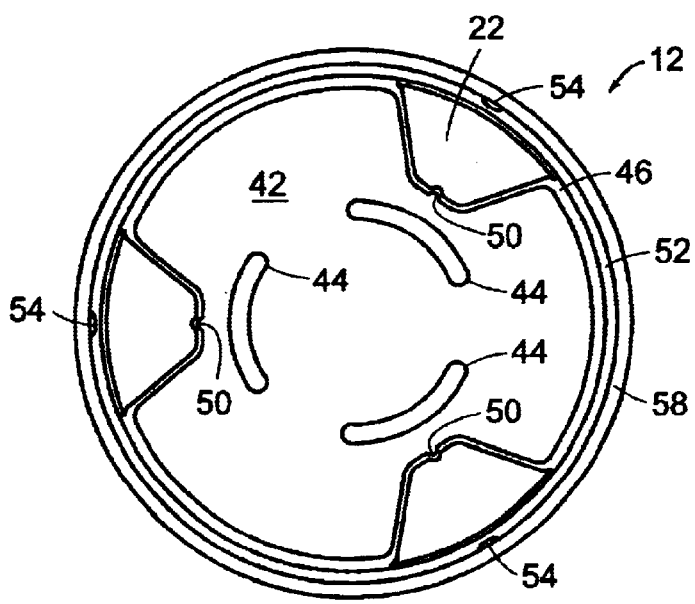
FIGS. 2 and 3 are a plan view and cross-sectional view of a well-defining base.
Figure 3:
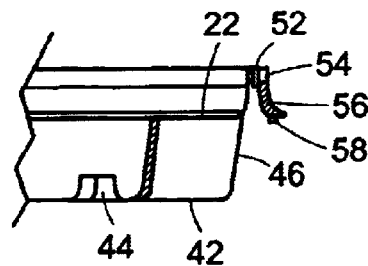
Figure 6:
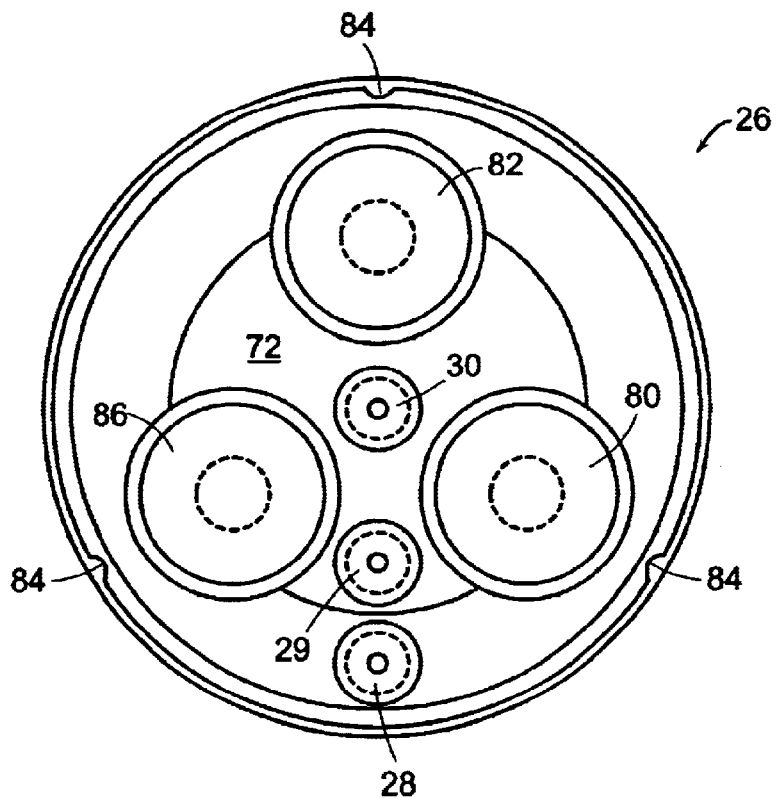
FIG. 6 is a plan view of a lid according to a first embodiment of the present invention.

FIGS. 2 and 3 show base (12) for defining a well for nutrients and for supporting a dish for holding the cells or tissues being cultured. Base (12) is preferably formed of a monolithic piece of molded plastic and includes a floor (42) with three slightly elevated support ribs (44), and an outer sidewall (46) that has three radially inwardly extending portions that form the walls of shelves (22). Wall (46) has at least one small indentation that can be used to orient the base (40) with respect to the lid (FIG. 6). Each of shelves (22) as a small notch (50) at its inner radial end. At the top of sidewall (46), a flange (52) extends radially outwardly then has a downwardly extending portion (56) tapering outwardly and an outwardly extending portion (56) tapering outwardly and an outwardly extending portion (58). Flange (52) also has small notches (54) at the top distributed (preferably evenly) around flange (52). For perspective, the overall diameter may be about 14–15 cm.

Figure 4:
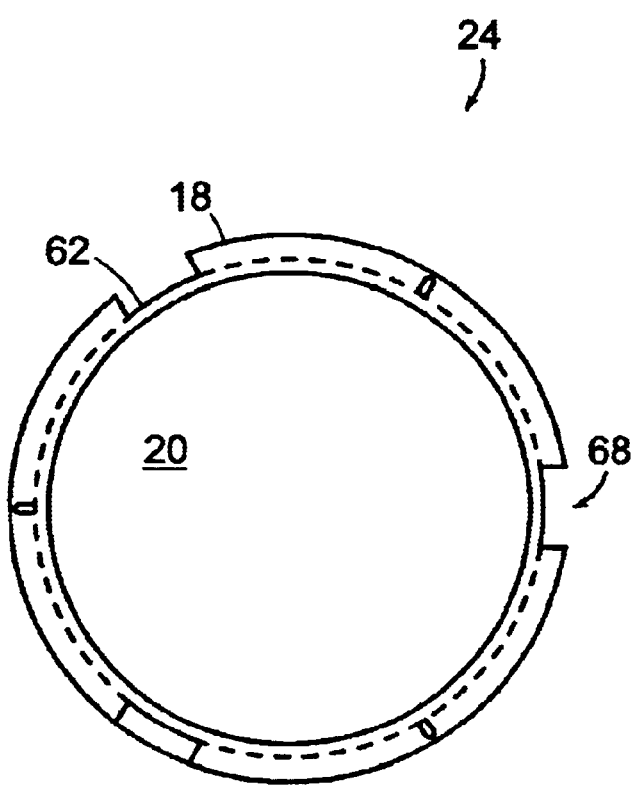
FIGS. 4 and 5 are a plan view and cross-sectional view of a dish according to the present invention.
Figure 5:
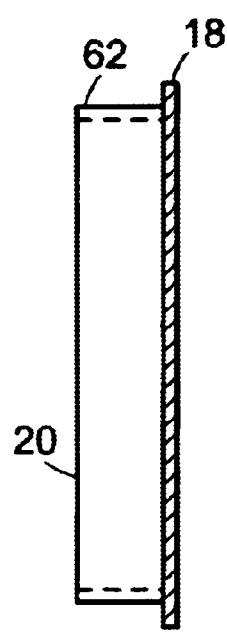

Referring to FIGS. 4 and 5, a dish (24) for holding biological material to be cultured has a sidewall (62), flange (18), and membrane (20). Flange (18), which may have cut-out notches (68), rests on shelves (22) of the base (12) shown in FIGS. 2 and 3. When in the base, membrane (66) is just above the top of support ribs (44). By putting nutrients into the well created by base (12), the nutrients can pass through membrane (20) to biological material. The sidewall and flange may be a monolithic plastic molded body, and the membrane may be made of polycarbonate.

Referring to FIG. 6, lid (26) has a substantially flat portion (72) and ports (28, 29, and 30). These ports are oriented along a radius of lid (26) with port (30) at the center of lid (26), port (28) near the outer edge, and port (29) therebetween. Lid (26) supports gas permeable membranes (80, 82 and 86), preferably made of HDPE as identified above with reference to FIG. 1. When lid (26) is provided over dish (24) and the dish is over the well, port (30) is located over the center of the dish, port (28) is at the outer edge of the membrane of the dish, and port (29) is over a portion of the well and not over the dish. Gas permeable membranes (80, 82, and 86) are positioned such that they are partly over the well and over the dish and partly not over the dish. At the outer end of lid (26), a rim extends upwardly, horizontally outwardly, downwardly, then horizontally outwardly. The outer diameter also has notches (84) formed in that outer flange. The size of the rim in the lid is sized and configured to form a snug frictional fit over flange (52) of base (12), and notches (84) are sized to mate with notches (54).

Figure 7:
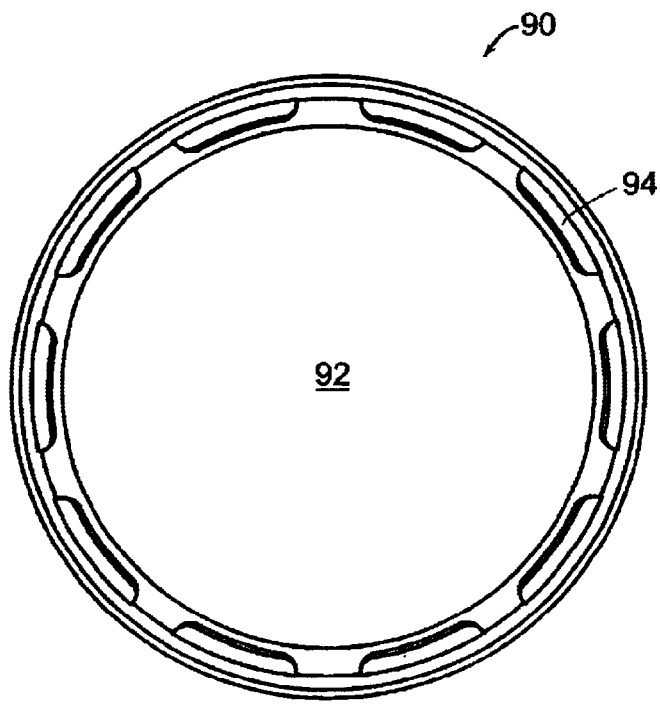
FIG. 7 is a plan view of an outer cover according to the present invention.

Referring to FIG. 7, an outer cover (90) is a monolithic plastic molded piece that has a substantially flat upward portion (92) and an outer end with recessed portions (94) extending about the outer diameter which provide stability and support. This outer lid fits over lid (26) for storage or other longer periods of inactivity.

Figure 8:
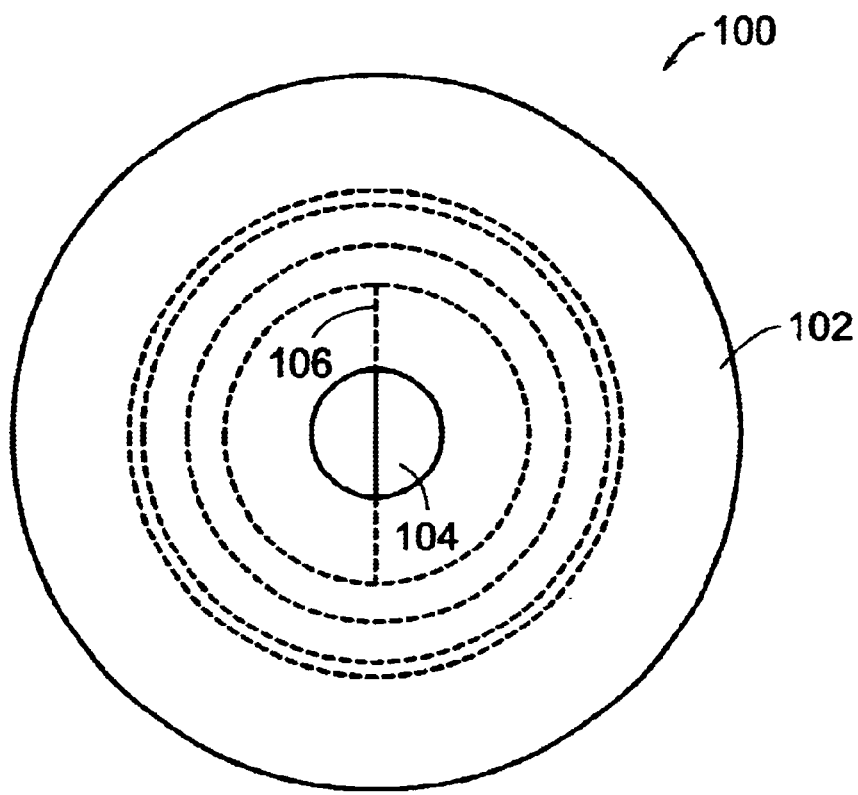
FIGS. 8 and 10 are plan views of two embodiments of septa.
Figure 9:
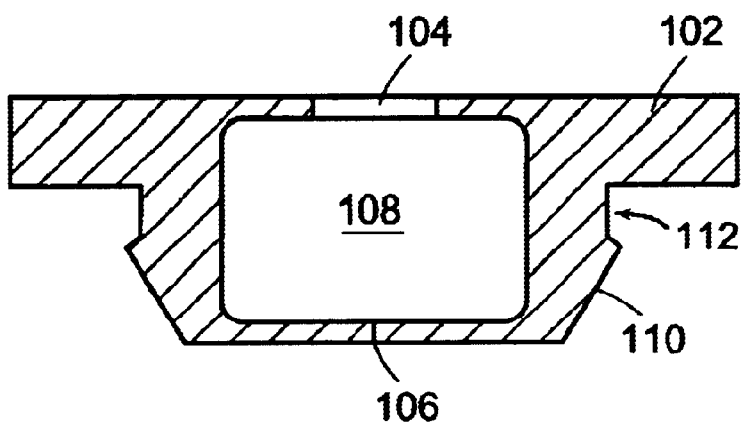
FIGS. 9 and 11 are respective cross-sectional views of those septa.

FIGS. 8–11 show two embodiments of ports, such as ports (28, 29, and 30) (FIG. 6). Referring to FIGS. 8 and 9 in conjunction with FIG. 6, a first type of port (100) is made of a soft and flexible silicone with a large diameter portion (102) at the top for resting on the top of lid (70). At the top of port (100) is an opening (104) and at the bottom is a single slit (106). The bottom could be an x-shaped double slit.

Between opening (104) and slit (106) is a cavity (108). Port (100) has a reduced diameter portion (112) with an axial length about equal to the thickness of lid (70), and a downward and inwardly tapered surface (10). Lid (70) has openings with a diameter the size of reduced diameter portion (112). Port (100) is sufficiently flexible so that it can be pushed through that hole as the tapered portion will compress until the lid snaps into reduced diameter portion (112).

The slit at the bottom of the port helps to prevent liquid and gas from escaping. A tube, such as a needle, nozzle, or syringe, slightly larger in diameter than opening (104) is used to provide material into or extracted out of the dish or the well. As the tube is inserted into the port, it forms a tight fit with the flexible plastic around opening (104), thus maintaining a good seal as it is inserted and withdrawn.

Figure 10:
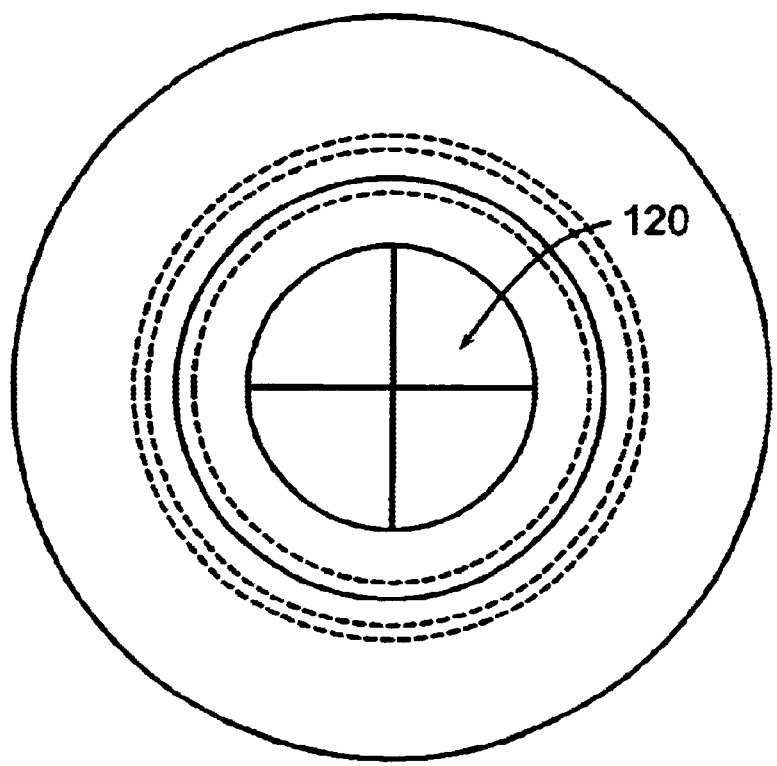
Figure 11:
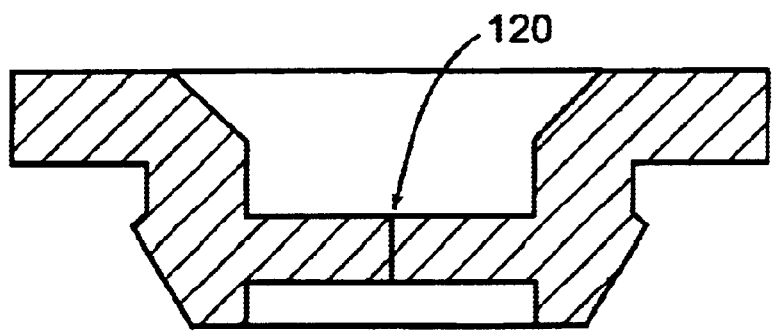

Referring to FIGS. 10 and 11, another variation of a port is shown. In this embodiment, the bottom has an x-shaped opening (120) that can seal around a tube used to introduce or remove liquid.

Figure 12:
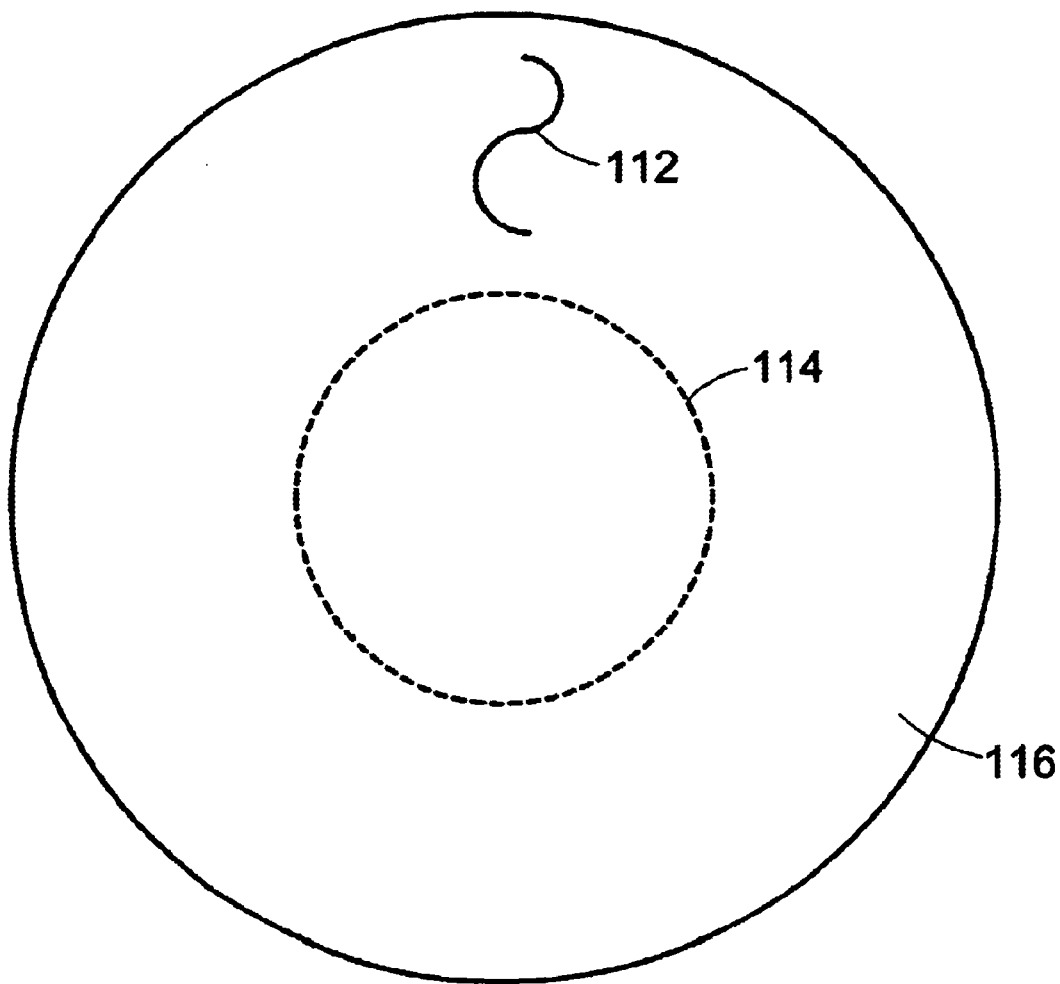
FIG. 12 is a plan view of a gas permeable membrane for use in the lid.

FIG. 12 shows a gas permeable membrane. The membrane is heat sealed at a sealing region (112). The dotted line (114) defines the areas of the membrane that is accessible across the membrane. The annular region (116) is a portion where the plastic lid covers the membrane (80, 82 and 86).

The bioreactor of the present invention can be used to perform or process a number of different kinds of biological materials. One application is in the formation of living skin equivalent (LSE). To make LSE, human dermal cells (fibroblasts) are combined with collagen, the primary protein of skin. The fibroblasts move through the collagen, rearranging it, while also producing human collagen. After this, human epidermal cells are placed on top of the dermal layer to cover it. Several days later, the epidermal cells are prompted by exposure to air to complete formation of an outer protective layer of skin, known as the stratum corneum. These cells are provided and processed on the membrane in the dish while nutrients-provided in the well help to support this process.

The system of the present invention allows for more convenient automation to insert and remove biological materials from the ports in the lid without requiring that the lid be removed, and without requiring significant labor, unlike typical current processes. In an automated system, bioreactors could be transported on a conveyor or with mechanical handling equipment that can move the bioreactors from one location to another. Using robotics or with x-y-z movement machines, syringes or other nozzles can be moved into and out of the bioreactor to insert or remove material. An x-y-z movement machine can have three different motors, one for movement in each of three orthogonal directions, and can include different types of motors and drives, such as a drive screw.

Having described the embodiment of the present invention, it should be apparent that modifications can be made without departing from the scope of the invention as defined by the appended claims. For example, the shapes and sizes of portions can be varied, as can the numbers of parts such as shelves, ports, and membranes. Certain items identified in embodiments here as monolithic could be formed from multiple pieces and loosely or integrally connected together.

What is claimed is:

1. A bioreactor system comprising:
    a base defining a well for holding nutrients;
    a dish supported in the base and having a membrane for holding biological material such that the material is in contact with the nutrients;
    a lid covering the well and the dish, the lid having a sealing port accessible with a tube for introducing or removing biological material from the dish and/or nutrients from the well, the port being sealed closed when a tube is not introduced.

2. The bioreactor of claim 1, wherein the lid has a plurality of ports at different radial locations.

3. The bioreactor of claim 1, further comprising one or more gas permeable membranes in the lid.

4. The bioreactor of claim 3, wherein the one or more membranes are made of high density polyethylene.

5. The bioreactor of claim 1, wherein the tube is a syringe.

6. The bioreactor of claim 1, wherein the tube is a pipette.

7. The bioreactor of claim 1, wherein the port is directly over the dish.

8. The bioreactor of claim 1, wherein the port is directly over the well and not directly over the dish.

9. The bioreactor of claim 1, wherein there is a plurality of ports, one of which is located over the dish and another of which is located over a portion of the well and not over the dish.

10. The bioreactor of claim 1, wherein the port automatically seals around the tube when the tube is inserted in the port.

11. A bioreactor system comprising:
    a base defining a well for holding nutrients;
    a dish supported in the base and having a membrane for holding biological material such that the material is in contact with the nutrients; a lid covering the well and the dish, the lid having a moisture barrier gas permeable membrane in the lid and a sealing port accessible with a tube for introducing or removing biological material from the dish and/or nutrients from the well, the port being sealed closed when a tube is not introduced.

12. The bioreactor of claim 11, wherein the lid has two or more moisture barrier gas permeable membranes.

13. The bioreactor of claim 11, wherein the membrane includes high density polyethylene.

14. The bioreactor of claim 11, wherein one membrane is located partly over the dish and partly over the well and not over the dish.

15. The bioreactor of claim 11, wherein a plurality of membranes are located partly over the dish and partly over the well and not over the dish.

16. The system of claim 11, wherein the membrane has an annular region for bonding to the lid and a central region not bonded to the lid.

17. A method comprising:

providing a well with nutrients;

providing biological material into a dish that is supported in a base over the well, the dish including a membrane on which the material is supported and that allows the nutrients to interact with the biological material;

covering the well and base with a lid having a sealing port; and using a tubular member to insert or remove biological material and/or nutrients through the port without removing the lid.

18. The method of claim 17, wherein the ports are sealed closed when the tubular member is not in the port, the port sealing around the tubular member when the tubular member is in the port.

19. The method of claim 17, wherein the tubular member is moved into and out of the port in an automated manner.

* * * * *